(12) United States Patent
Ahlman et al.

(10) Patent No.: US 10,548,699 B2
(45) Date of Patent: Feb. 4, 2020

(54) DRIVE TRAIN ASSEMBLY FOR A PERSONAL CARE DEVICE

(71) Applicant: KONINKLIJKE PHILIPS N.V., Eindhoven (NL)

(72) Inventors: Dave Ahlman, Bothell, WA (US); Wolter F. Benning, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/769,918

(22) PCT Filed: Aug. 2, 2017

(86) PCT No.: PCT/EP2017/069485
§ 371 (c)(1),
(2) Date: Apr. 20, 2018

(87) PCT Pub. No.: WO2018/024752
PCT Pub. Date: Feb. 8, 2018

(65) Prior Publication Data
US 2019/0365518 A1    Dec. 5, 2019

Related U.S. Application Data

(60) Provisional application No. 62/370,262, filed on Aug. 3, 2016.

(51) Int. Cl.
*H02K 33/00* (2006.01)
*A61C 17/34* (2006.01)
(Continued)

(52) U.S. Cl.
CPC .......... *A61C 17/3418* (2013.01); *F16C 11/00* (2013.01); *H02K 7/003* (2013.01); *H02K 7/083* (2013.01); *H02K 33/02* (2013.01)

(58) Field of Classification Search
CPC .......... H02K 7/085; H02K 7/08; H02K 7/003; H02K 7/083; H02K 33/02; A61C 17/3418;
(Continued)

(56) References Cited

U.S. PATENT DOCUMENTS 2,439,262 A * 4/1948 Gresham ............ A61C 17/3436
62/414
4,827,550 A * 5/1989 Graham .................. A46B 3/06
15/22.1
(Continued)

FOREIGN PATENT DOCUMENTS

CN        201727599 U    2/2011
EP          2407124 A1    1/2012
(Continued)

*Primary Examiner* — Thanh Lam

(57) ABSTRACT

A drive train assembly (22) for a personal care device (10), the drive train assembly including a shaft (24) with a central axis and a plurality of pivot bearing notches (122); a motor (130) encircling at least a portion of the shaft and configured to oscillate the shaft about the shaft's central axis; and a plurality of stationary pivot bearings (120), where at least an apex of each of the plurality of stationary pivot bearings is positioned within a respective one of the plurality of pivot bearing notches.

15 Claims, 8 Drawing Sheets

(51) Int. Cl.
*H02K 7/00* (2006.01)
*F16C 11/00* (2006.01)
*H02K 33/02* (2006.01)
*H02K 7/08* (2006.01)

(58) Field of Classification Search
CPC .. A61C 17/3427; A61C 17/3436; F16C 11/00
USPC ........ 310/15, 21, 25, 29, 33, 36, 37, 38, 50, 310/81, 90
See application file for complete search history.

(56) References Cited

U.S. PATENT DOCUMENTS

| | | |
|---|---|---|
| 8,256,055 B2 | 9/2012 | Kressner |
| 8,418,302 B1 | 4/2013 | Suen |
| 9,289,799 B2 | 3/2016 | Kleibl et al. |
| 2012/0024323 A1* | 2/2012 | Klemm ................. A61C 17/22 134/18 |
| 2016/0067011 A1* | 3/2016 | Rothenwaender ..... A61C 1/148 433/124 |
| 2019/0038011 A1* | 2/2019 | Diamond ............. A46B 5/0058 |

FOREIGN PATENT DOCUMENTS

| | | |
|---|---|---|
| WO | 2012020351 A2 | 2/2012 |
| WO | 2015159250 A1 | 10/2015 |
| WO | 2016009368 A1 | 1/2016 |

* cited by examiner

DRIVE TRAIN ASSEMBLY FOR A PERSONAL CARE DEVICE

CROSS-REFERENCE TO PRIOR APPLICATIONS

This application is the U.S. National Phase application under 35 U.S.C. § 371 of International Application No. PCT/EP2017/069485, filed on Aug. 2, 2017 which claims the benefit of U.S. Provisional Patent Application No. 62/370,262, filed on Aug. 3, 2016. These applications are hereby incorporated by reference herein.

FIELD OF THE INVENTION

The present disclosure is directed generally to a personal care device drive train configuration using pivot bearings to suspend the drive train shaft about its axis.

BACKGROUND

Proper tooth brushing, including length and coverage of brushing, helps ensure long-term dental health. Many dental problems are experienced by individuals who either do not regularly brush their teeth or who do so inadequately, especially in a particular area or region of the oral cavity. Among individuals who do brush regularly, improper brushing habits can result in poor coverage of brushing and thus surfaces that are not adequately cleaned during a cleaning session, even when a standard brushing regimen is followed. Electric cleaning devices, such as electric toothbrushes, have been shown to greatly increase the efficacy of a cleaning session.

These electric cleaning devices, including power toothbrushes, shavers, and similar devices, have a motor, such as a mechanical, electromechanical, magnetic motor, that engages a drive train in order to drive a brushhead in an oscillating, reciprocating, or other pattern. The high-speed oscillating movement of the drive train shaft of the device requires special bearings to constrain motion to only rotation about the center axis. However, existing bearings are not perfectly suited for the high-speed oscillating movement of the drive train shaft. For example, although sleeve bearings are simple and cheap, they are problematic due to power loss from friction and from rattling between the shaft and bearing. Ball bearings have low friction, but are not well-suited to oscillating movement due to poor distribution of lubrication and need for axial loading to reduce noise. In addition, ball bearings are complex and expensive. None of the existing bearings utilized in these specialized drive trains achieve the goal of being quiet, low-cost, low-friction, and simple.

Accordingly, there is a continued need for personal care devices with drive trains having bearings that constrain motion to only rotation about the center axis, and are quiet, inexpensive, and low-friction.

SUMMARY OF THE INVENTION

The present disclosure is directed to inventive drive train assemblies comprising a central oscillating shaft constrained about its central rotational axis by one or more pivot bearings. Applied to an electric or power personal care device such as an electric toothbrush or shaver, the inventive systems provide a highly efficient drive train assembly with very low friction, since the pivot bearings focus all radial forces to a small surface area at the shaft's central axis. The drive train assembly is also very quiet, since the only moving part is the oscillating shaft.

Generally in one aspect, a drive train assembly for a personal care device is provided. The drive train assembly includes: a shaft comprising a central axis and a plurality of pivot bearing notches; a motor encircling at least a portion of the shaft and configured to oscillate the shaft about the shaft's central axis; and a plurality of stationary pivot bearings, wherein at least an apex of each of the plurality of stationary pivot bearings is positioned within a respective one of the plurality of pivot bearing notches.

According to an embodiment, a first subset of the plurality of stationary pivot bearings is positioned at a first end of the motor, and a second subset of the plurality of stationary pivot bearings is positioned at a second end of the motor.

According to an embodiment, the first subset and second subset each comprises three pivot bearings positioned around the shaft, and the apex of each of the three pivot bearings is offset by approximately 120 degrees from the apex of the neighboring pivot bearings.

According to an embodiment, the apex of each of the plurality of pivot bearing notches is positioned at the shaft's central axis.

According to an embodiment, the drive train assembly further includes a first pivot bearing frame located at a first end of the motor and a second pivot bearing frame located at a second end of the motor, the first pivot bearing frame and the second pivot bearing frame each comprising a plurality of pivot frame notches, wherein each of the plurality of pivot frame notches is configured to align with one of the plurality of pivot bearing notches.

According to an embodiment, each of the plurality of pivot frame notches comprises a locking mechanism configured to affix the pivot bearing in place.

According to an embodiment, the first and second pivot bearing frames each comprise a plurality of pivot bearing frame plates.

According to an embodiment, the apex of the pivot bearing is pointed or curved.

According to an embodiment, the pivot bearing is a butterfly clip.

According to an embodiment, the drive train assembly further includes a magnetic force exerted on the shaft, the direction of the magnetic force opposing the forces exerted by the plurality of pivot bearings on the shaft.

According to an aspect is a personal care device. The personal care device includes a housing, and a drive train assembly, the drive train assembly including a shaft comprising a central axis and a plurality of pivot bearing notches; a motor configured to oscillate the shaft about the shaft's central axis; and a plurality of stationary pivot bearings, where at least an apex of each of the plurality of stationary pivot bearings is positioned within a respective one of the plurality of pivot bearing notches.

According to an aspect is a drive train assembly for a personal care device. The drive train assembly includes a shaft comprising a central axis and a plurality of pivot bearing notches, wherein the apex of each of the plurality of pivot bearing notches is positioned at the shaft's central axis; a motor encircling at least a portion of the shaft and configured to oscillate the shaft about the shaft's central axis; a first pivot bearing frame located at a first end of the motor and comprising a first plurality of pivot frame notches; a second pivot bearing frame located at a second end of the motor and comprising a second plurality of pivot frame notches, wherein each of the first and second plurality of pivot frame notches is configured to align with one of the plurality of pivot bearing notches; and a plurality of stationary pivot bearings, wherein at least an apex of each of the plurality of stationary pivot bearings is positioned within a respective one of the plurality of pivot bearing notches, wherein a first subset of the plurality of stationary pivot bearings are positioned at a first end of the motor, and further wherein a second subset of the plurality of stationary pivot bearings are positioned at a second end of the motor.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a device for a drive train assembly for an electric personal care device. More generally, Applicant has recognized and appreciated that it would be beneficial to provide a one- or two-piece spring assembly that is more efficient and more resistant to stress. Accordingly, the systems described or otherwise envisioned herein provide a personal care device, such as an electric toothbrush or shaver, with a drive train comprising a central oscillating shaft constrained about its central rotational axis by one or more pivot bearings.

The present disclosure describes various embodiments of a device for a drive train assembly for an electric personal care device. More generally, Applicant has recognized and appreciated that it would be beneficial to provide a drive train assembly with improved bearings to decrease friction and noise levels. Accordingly, the systems described or otherwise envisioned herein provide a personal care device, such as an electric toothbrush or shaver, with a drive train assembly comprising a central oscillating shaft constrained about its central rotational axis by one or more pivot bearings. According to an embodiment, the pivot bearings of the drive train spring assembly focus all radial forces to a small surface area at the shaft's central axis, resulting in very low friction and noise due to very few moving parts.

A particular goal of utilization of the embodiments and implementations herein is to provide a drive train assembly for an oral care device such as, e.g., a Philips Sonicare™ toothbrush (manufactured by Koninklijke Philips Electronics, N.V.), although the assembly may be utilized with many other personal care devices, including tongue scrapers, flossers, shavers, skin cleaners, and many other devices.

Figure 1:
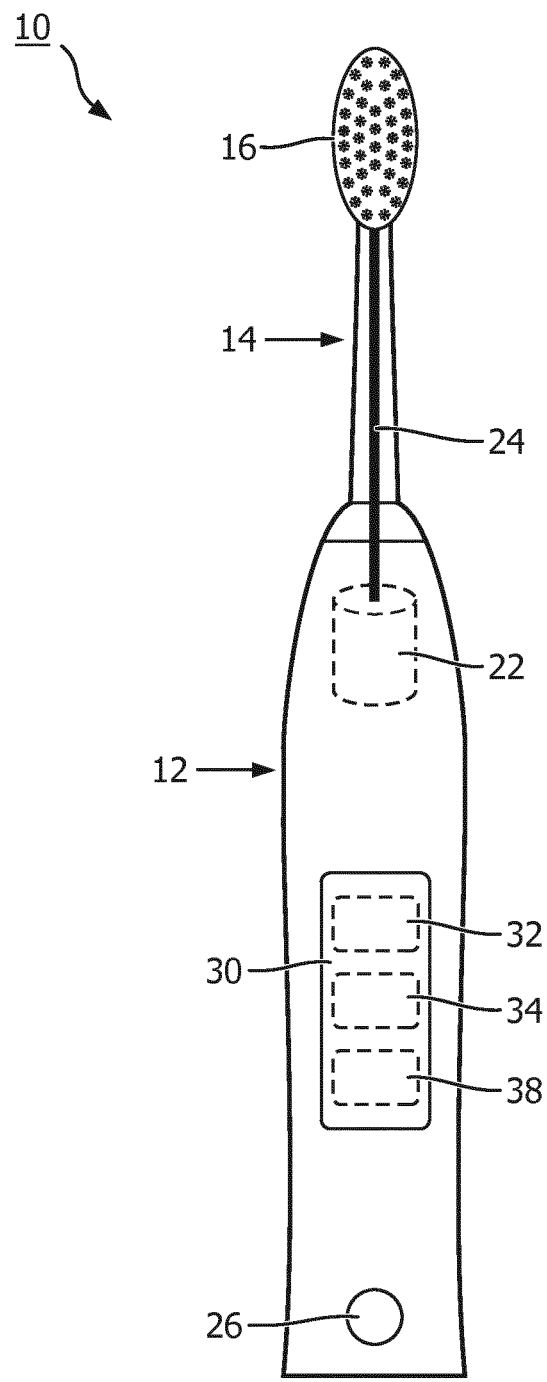
FIG. 1 is a schematic representation of a personal care device, in accordance with an embodiment.

Referring to FIG. 1, in one embodiment, a personal care device 10 is provided that includes a body portion with a housing 12 and a brush head member 14 mounted on the body portion. Brush head member 14 includes at its end remote from the body portion a brush head 16.

Head member 14 is mounted so as to be able to move relative to the body portion housing 12. The movement can be any of a variety of different movements, including vibrations or rotation, among others. According to one embodiment, head member 14 is mounted to the body so as to be able to vibrate relative to body portion housing 12, or, as another example, brush head 16 is mounted to brush head member 14 so as to be able to vibrate relative to body portion housing 12. The brush head member 14 can be fixedly mounted onto body portion housing 12, or it may alternatively be detachably mounted so that head member 14 can be replaced with a new one when the bristles or another component of the device are worn out and require replacement.

The body portion housing incorporates a drive train 22 for generating movement and a transmission component, or shaft 24, for transmitting the generated movements to brush head member 14. For example, drive train assembly 22 comprises a motor or electromagnet(s) that generates movement of a drive train shaft 24, which is subsequently transmitted to the brush head member 14. Drive train assembly 22 can include components such as a power supply, an oscillator, and one or more electromagnets, among other components. In this embodiment the power supply comprises one or more rechargeable batteries, not shown, which can, for example, be electrically charged in a charging holder in which oral cleaning device 10 is placed when not in use.

The body portion housing is further provided with a user input 26 to activate and de-activate drive train 22. The user input 26 allows a user to operate the personal care device 10, for example to turn the personal care device 10 on and off. The user input 26 may, for example, be a button, touch screen, or switch.

The body portion housing of the device also comprises a controller 30. Controller 30 may be formed of one or multiple modules, and is configured to operate the personal care device 10 in response to an input, such as input obtained via user input 26. Controller 30 can comprise, for example, a processor 32 and a memory 34, and can optionally include a connectivity module 38. The processor 32 may take any suitable form, including but not limited to a microcontroller, multiple microcontrollers, circuitry, a single processor, or plural processors. The memory 34 can take any suitable form, including a non-volatile memory and/or RAM. The non-volatile memory may include read only memory (ROM), a hard disk drive (HDD), or a solid state drive (SSD). The memory can store, among other things, an operating system. The RAM is used by the processor for the temporary storage of data. According to an embodiment, an operating system may contain code which, when executed by controller 30, controls operation of the hardware components of personal care device 10. According to an embodiment, connectivity module 38 transmits collected sensor data, and can be any module, device, or means capable of transmitting a wired or wireless signal, including but not limited to a Wi-Fi, Bluetooth, near field communication, and/or cellular module.

Figure 2:
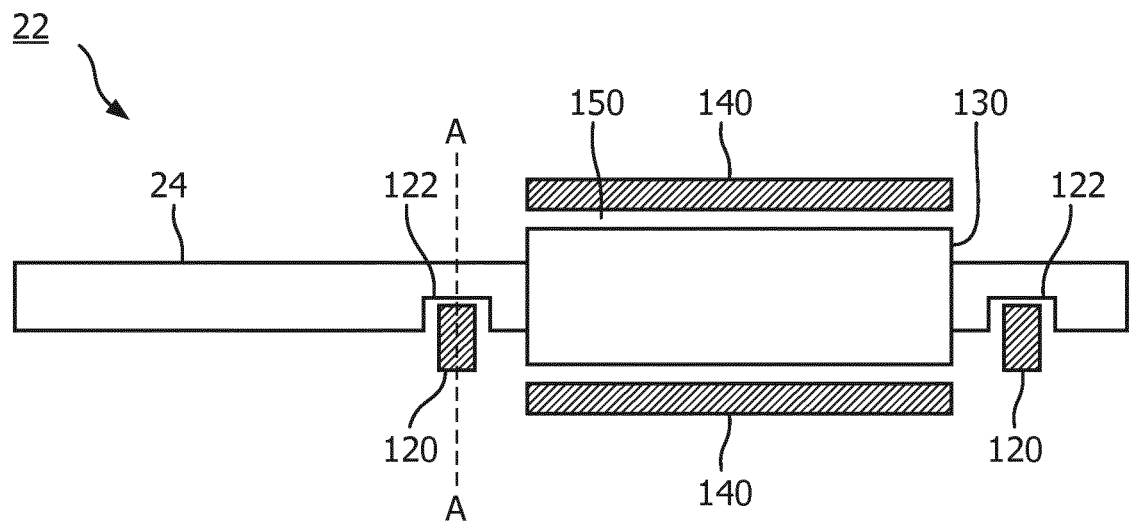
FIG. 2 is a schematic representation of a drive train assembly of a personal care device, in accordance with an embodiment.

Referring to FIG. 2, in one embodiment, is a drive train assembly 22 with a shaft 24 and a motor or drive 130. The drive 130 surrounds the shaft 24 and causes the shaft to rotate around its central axis (as shown by the arrow in FIG. 3). The shaft comprises or defines one or more notches 122, into each of which a pivot bearing 120 is positioned. The notches 122 each comprise bearing contact surfaces that interact with the surfaces of the pivot bearing 120. According to an embodiment, each pivot bearing 120 provides a contact at the center line of motion. The pivot bearings 120 remain stationary while the shaft 24 rotates back and forth around its lengthwise central axis. Although the shaft is depicted as generally round, it could easily be square, flat or a more complex form. Even the motor could be configured to be square, or any other shape.

Figure 3:
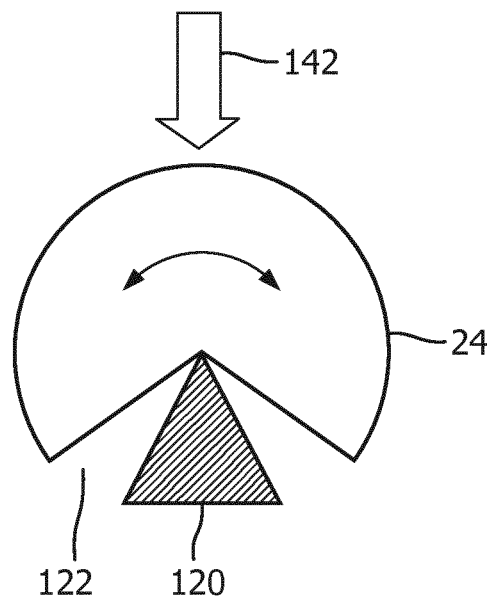
FIG. 3 is a cross-section of the drive train assembly of FIG. 2 at axis A-A, in accordance with an embodiment.

Drive train assembly 22 optionally comprises one or more magnets 140 which provide a radial preload force, as shown by arrow 142 in FIG. 3. The preload force is provided through the magnetic offset in the motor 130. As shown in FIG. 2, magnets are positioned at both sides of the motor. The airgap 150 between the motor 130 and the one or more magnets at the bearing side can be smaller than the opposite side, and therefore can have a higher magnetic attraction force. According to this embodiment, the preload force presses the shaft 24 onto the pivot bearing or bearings 120, and thereby locks in both radial degrees of freedom, both through the contact shape and radial friction in the bearing point. With the bearings this controls four degrees of freedom, and thereby allows free axial rotation and axial motion. The preload force is preferably designed such that it is not overcome by bearing forces resulting from normal user brushing forces, which might create a clearance leading to noise and wear. The orientation of the bearings and the preload relative to the main user-applied force load can be chosen for optimal performance. For example, depending upon orientation, the typical preload force may range from 10 to 40 Newton. Although FIG. 2 depicts both bearings 120 in the same orientation, another embodiment might have them oriented in opposing orientation, or numerous other possible orientations, in order to take up the load torque.

According to another embodiment, one or more mechanical springs may be utilized to provide the radial preload force, instead of one or more magnets. Other methods of applying the radial force are also possible.

Referring to FIG. 3, in one embodiment, is a cross-section of the shaft 24 and pivot bearing 120 along axis A/A in FIG. 2. The circular shaft comprises or defines a generally triangular notch 122 into which pivot bearing 120 is positioned. The apex of the pivot bearing is positioned at the apex of the notch 122. The shaft 24 rotates about its central axis, and the two opposite sides of the notch 122 alternate interaction with a side of the pivot bearing 120.

Figure 4:
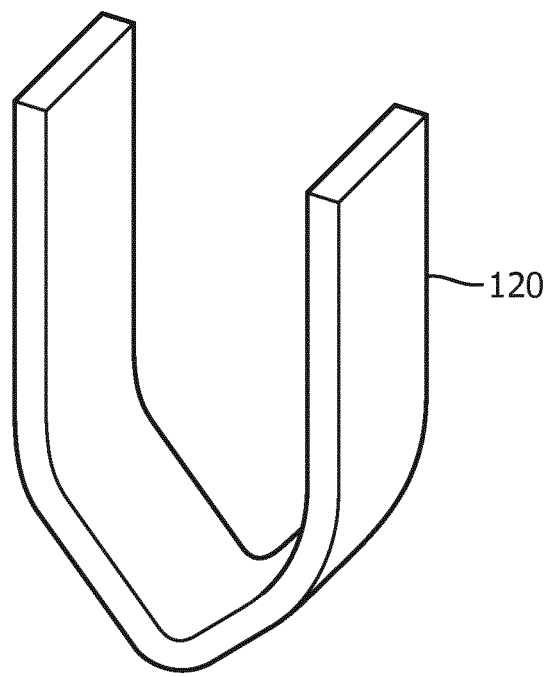
FIG. 4 is a schematic representation of a pivot bearing, in accordance with an embodiment.

Referring to FIG. 4, in one embodiment, the pivot bearing 120 is generally triangular and in the form of a clip. The pivot bearing 120 fits into a triangular notch 122 of the shaft 24, as discussed in greater detail below. This pivot bearing 120 can be, for example, stamped from steel or another metal and bent into the triangular "V" shape, with the apex contacting the shaft axis and the two ends locking into the frame of the personal care device. This design is low cost, accurate, and integrates a limited but sufficient degree of flexibility in the rotational and radial directions with respect to the shaft 24.

Figure 5:
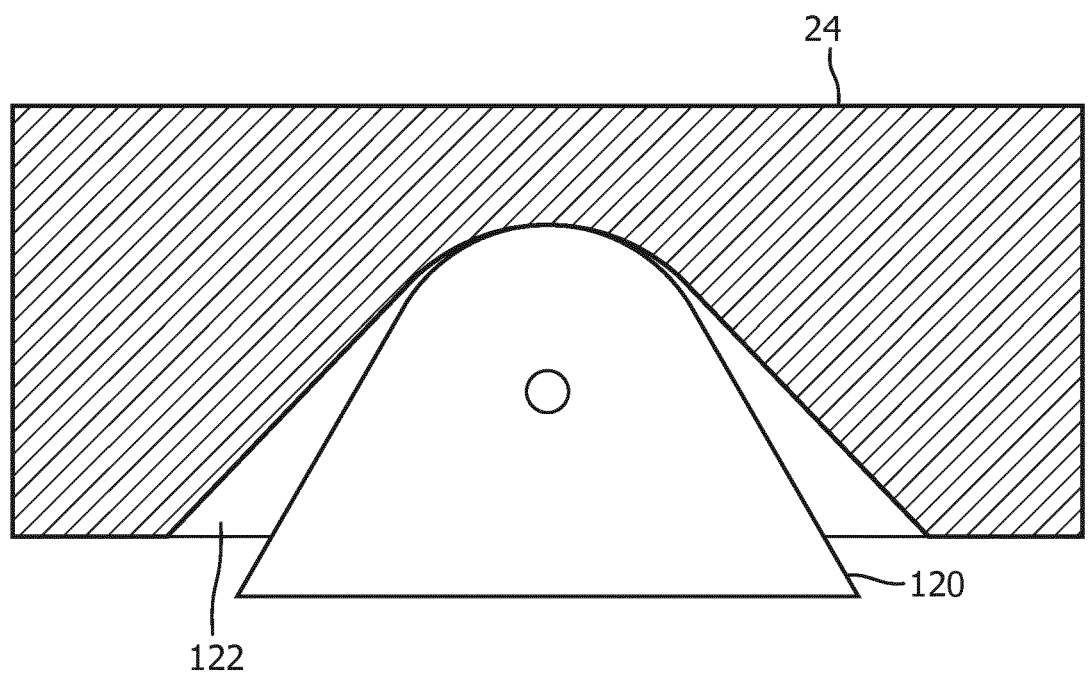
FIG. 5 is a cross-section of a shaft and pivot bearing, in accordance with an embodiment.

The pivot bearings 120 and notch 122 may take many different shapes in addition to the triangular shapes depicted in FIGS. 2-4. For example, referring to FIG. 5 is one embodiment of a pivot bearing 120. The apex of the pivot bearing 120 in FIG. 5 is rounded, which interacts with a similarly rounded portion of the notch 122 of shaft 24. For proper functioning, the notch 122 in the shaft will be designed or configured to comprise a complementary shape to the pivot bearing 120. The shaft will have a slightly larger curvature radius than the pivot bearing. The final radius dimensions depend on the strength of the specific material of the pivot bearing and shaft. This shape provides a near-stable center of motion at limited angular motion. The friction from the bearing preload provides side-to-side stability combined with form limitations for excessive loads. Although FIG. 5 depicts the pivot bearing 120 and the notch 122 as comprising a constant curvature, other curvature profiles are possible. For example, the pivot bearing 120 and/or notch 122 can comprise varying curvatures, both digressive and progressive, which might provide better dynamic stability in the application.

According to an embodiment, the pivot bearing can be self-centering to provide a virtual center with minimal shift at 5 degrees angular oscillation. The pivot bearing will preferably be low friction, but will not exhibit slip in normal use conditions. The contract stresses should be below the material fatigue stress levels of the material utilized for these portions of the drive shaft. Additionally, the pivot bearing should be sufficiently robust in order to prevent damage during drops or other user abuse.

Figure 6A:
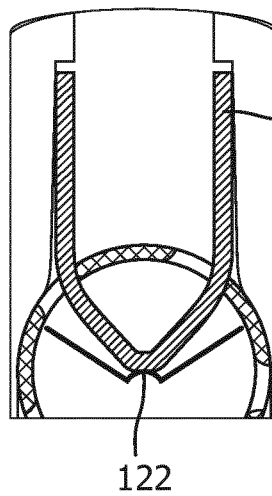
FIG. 6A is a cross-section of a shaft and pivot bearing, in accordance with an embodiment.
Figure 6B:
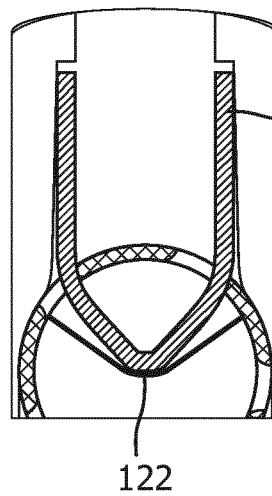
FIG. 6B is a cross-section of a shaft and pivot bearing, in accordance with an embodiment.
Figure 6C:
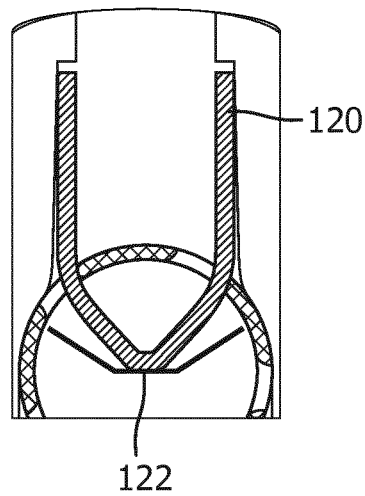
FIG. 6C is a cross-section of a shaft and pivot bearing, in accordance with an embodiment.

Similar to the pivot bearing 120, the shaft notches 122 can take a variety of shapes. In FIG. 3, the shaft notch is generally triangular. In FIG. 5, the shaft notch is generally curved. Referring to FIGS. 6A, 6B, and 6C, the shaft notches 122 can take a variety of shapes. In FIG. 6A, the shaft notch 122 comprises a peak at the center of the notch which interacts with the apex of the pivot bearing 120. In FIG. 6B, the shaft notch 122 comprises a valley at the center of the notch which interacts with the apex of the pivot bearing 120. In FIG. 6C, the shaft notch 122 comprises a flat region at the center of the notch which interacts with the apex of the pivot bearing 120. Many other shapes and configurations are possible. Each shape can have a different effect on friction, sound, stability, and/or performance. Selection is based on materials used, loads borne, required range of motion, and/or cost.

Figure 7A:
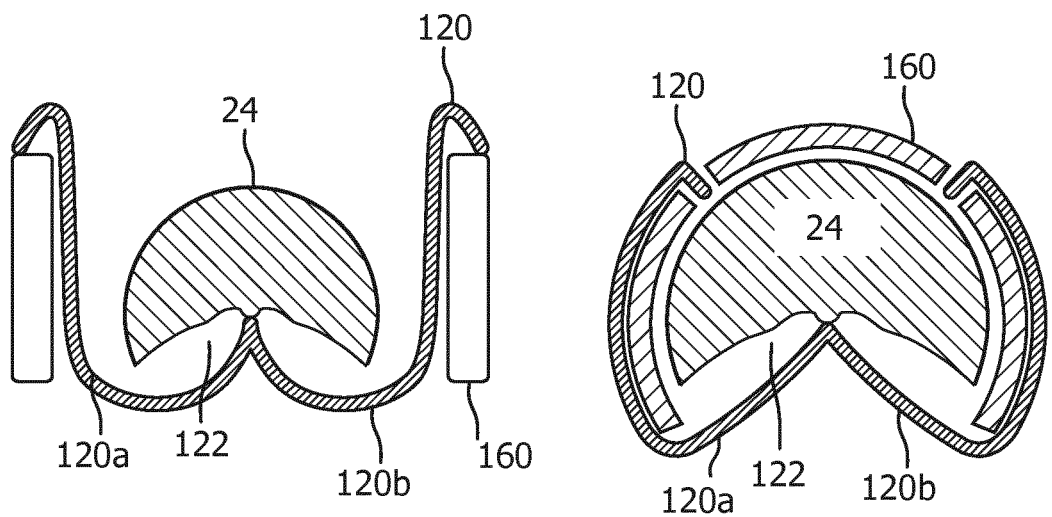
FIG. 7A is a cross-section of a shaft and pivot bearing, in accordance with an embodiment.
Figure 7B:
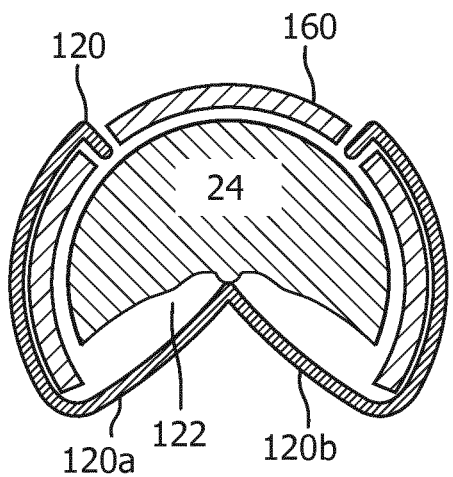
FIG. 7B is a cross-section of a shaft and pivot bearing, in accordance with an embodiment.

Referring to FIGS. 7A and 7B are two other embodiments of the shaft 24 and the pivot bearing 120, which in these configurations is a pivot bearing clip. The shaft comprises a notch 122 into which pivot bearing 120 is positioned. The pivot bearing comprises two arms 120a, 120b that engage other portions of the device or drive assembly. For example, in FIG. 7B, the arms of the pivot bearing 120 engage a frame 160 which encircles at least a portion of the shaft 24. The lengths of the side arms 120a, 120b of the pivot bearing clip 120 may be adjusted to meet requirements for stability and flexibility. The frame 160 to which the pivot bearing clip attaches also, therefore, may be adjusted to meet requirements for stiffness, reliability, and ease of assembly.

Figure 8:
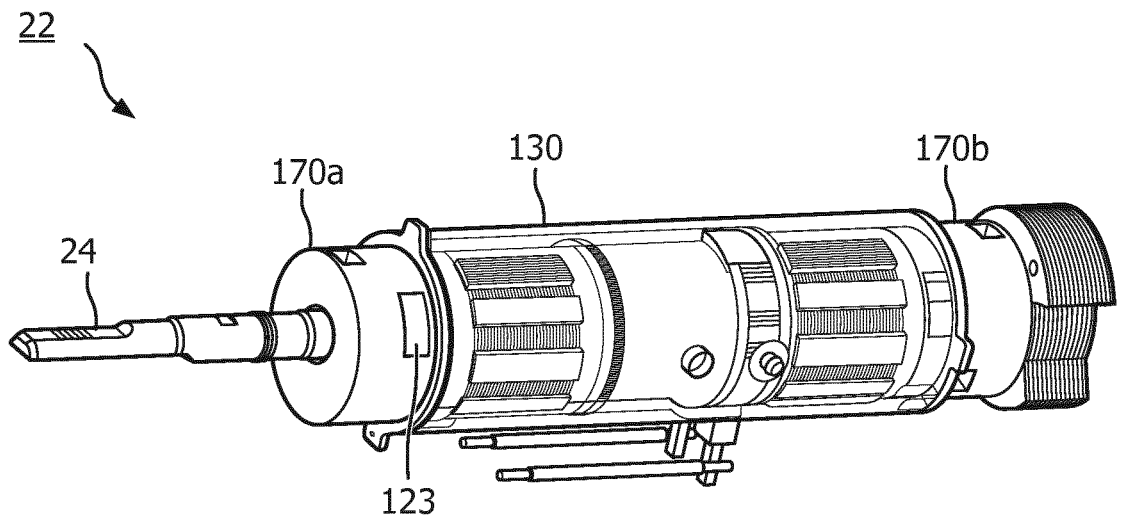
FIG. 8 is a schematic representation of a drive train assembly of an oral care device, in accordance with an embodiment.
Figure 9:
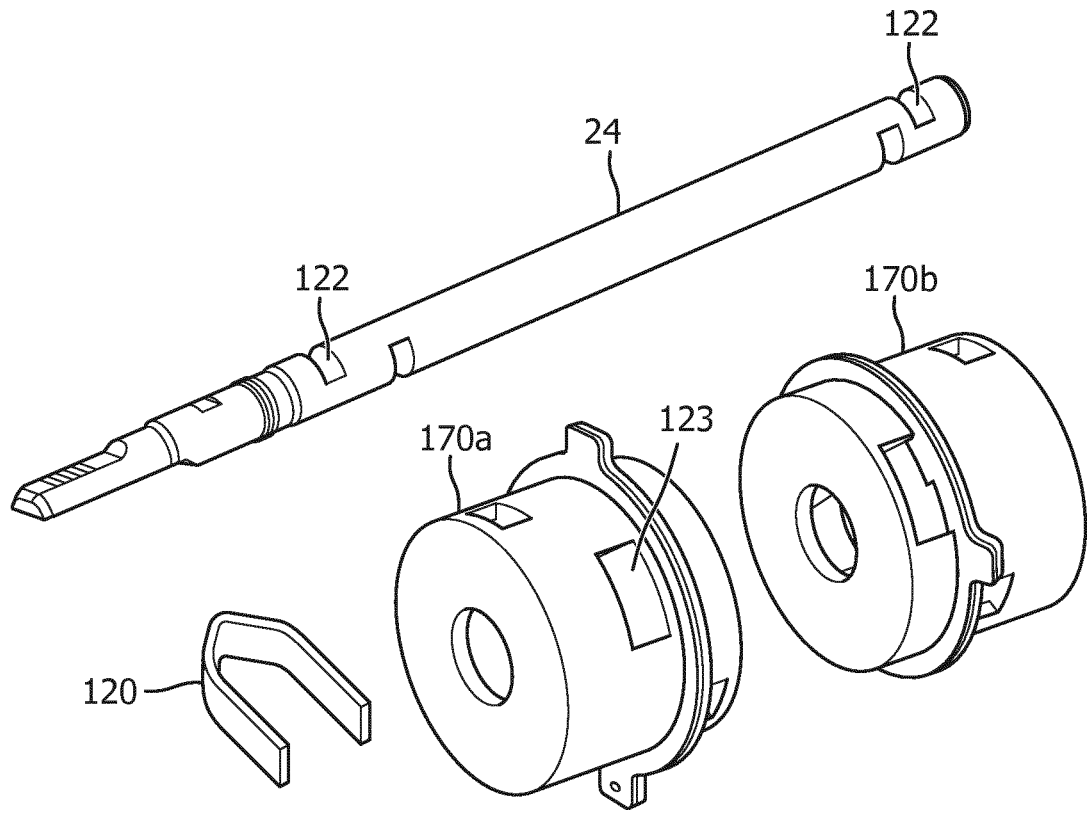
FIG. 9 is a schematic representation of the components of the drive train assembly of FIG. 8, in accordance with an embodiment.

Referring to FIGS. 8 and 9, in one embodiment, is a drive train assembly 22 with a shaft 24, a motor or drive 130, and two pivot frames 170a and 170b. FIG. 9 is a schematic representation of the component parts of the assembled drive train assembly 200 shown in FIG. 8. According to this embodiment, the shaft 24 comprises six (6) pivot bearing clips 120 which constrain the shaft about its central axis. Each of the six pivot bearing clips 120 engages, at its apex, a notch 122 formed in shaft 24. The six pivot bearing clips 120 can be stamped from steel and bent into proper shape. As the shaft rotates about its central axis, its exact central axis is a line of no motion. The pivot bearing clips 120 focus all radial forces to a small surface area at the shaft's central axis, and thus friction is very low and this suspension method is highly efficient. According to this embodiment, the shaft has six notches that expose its central axis, with three notches at either end. The three notches at either end can be offset, for example, by approximately 120 degrees from each other. The notches 122 are sufficiently large to accept the apex of the pivot bearing clips 120 and permit the designed range of rotation motion. Since the shaft bending strength is reduced by enlarging these notches, their size should be limited.

According to an embodiment, the shaft 24v can be a hard and stiff material like steel, although other metals are possible. It may start as a round cylinder that is machined to create notches, or it may start as a bar of any shape cross section that is a bent and formed to achieve the requisite contact surfaces. The shaft may also be formed by molding or forging and used as is, or may be machined to achieve required dimensional accuracy. The notches may be machined in two steps, with the first step being a rough grinding operation followed by an EDM element to form the precise geometry that exposes the shaft's central axis. For example, steel may be machined quickly and then hardened with accurate dimensions retained. Other methods of manufacturing the shaft 24 and shaft notches 122 are possible.

According to an embodiment, the design of drive train assembly 22 is ideal for the motion of an oscillating machine, where a quiet, low-friction suspension is needed for rotational movement up to 30 degrees (±15°). Friction is lower when rotation is restricted to smaller values, while larger rotations add to tangential forces between the suspension elements and shaft, resulting in possible friction and wear. A very small amount of rotational compliance in one or more of the suspension elements is a mediation measure for such friction and wear against the shaft. According to an embodiment, in order to ensure consistent and quiet operation, one or more of the bearings may have a radially flexible component that ensures constant contact against the shaft.

Figure 10:
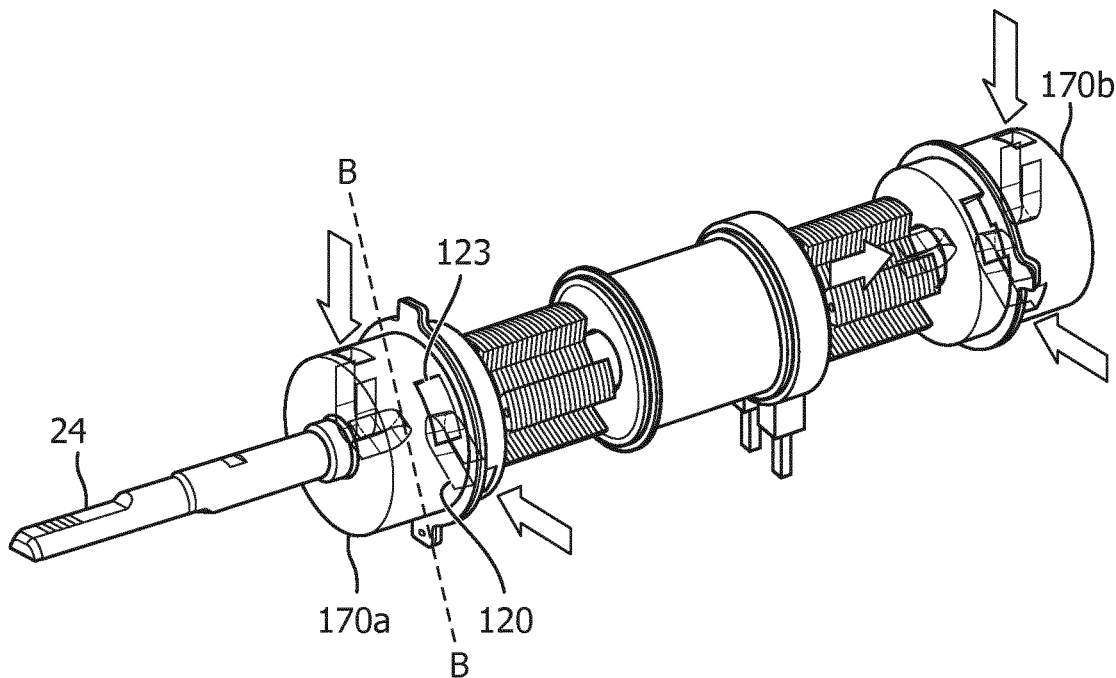
FIG. 10 is schematic representation of a drive train assembly of a personal care device, in accordance with an embodiment.

According to an embodiment, the two pivot frames 170a and 170b are stationary within the device and affix the six pivot bearing clips 120 in place to interact with the shaft notches 122. The pivot frames can be injection molded or composed of stacked laminations of stamped steel. For example, as shown in FIG. 10, the six pivot bearing clips 120 are inserted into notches 123 in the pivot frames, which positions the apex of the clips 120 into the notches 122 of the shaft 24. Although FIGS. 8-10 depicted six pivot bearing clips 120, other quantities of pivot bearings are possible. For example, there may be two, three, four, five, seven, eight, or any of a wide variety of other number of pivot bearing clips 120.

According to an embodiment, the pivot frame 170 may be manufactured in many ways. For example, at each end, two of the bearings may be integrated as rigid features in the frame. The shaft then rests on the two rigid pivot points on the frame at 0° and 120°, while the third contact point is the flexible suspension element located at 240°. This reduces the number of moving/flexible parts and improves manufacturing consistency. The assembly can be further simplified when the notches are formed in such a way as to permit entry of suspension elements at a radial entry angle normal to the bifurcated angle between the notches. To mold the frame, the molding tool may be shaped in such a way that it enters deeply in the radial direction to create the pass-through feature for the suspension element.

Figure 11:
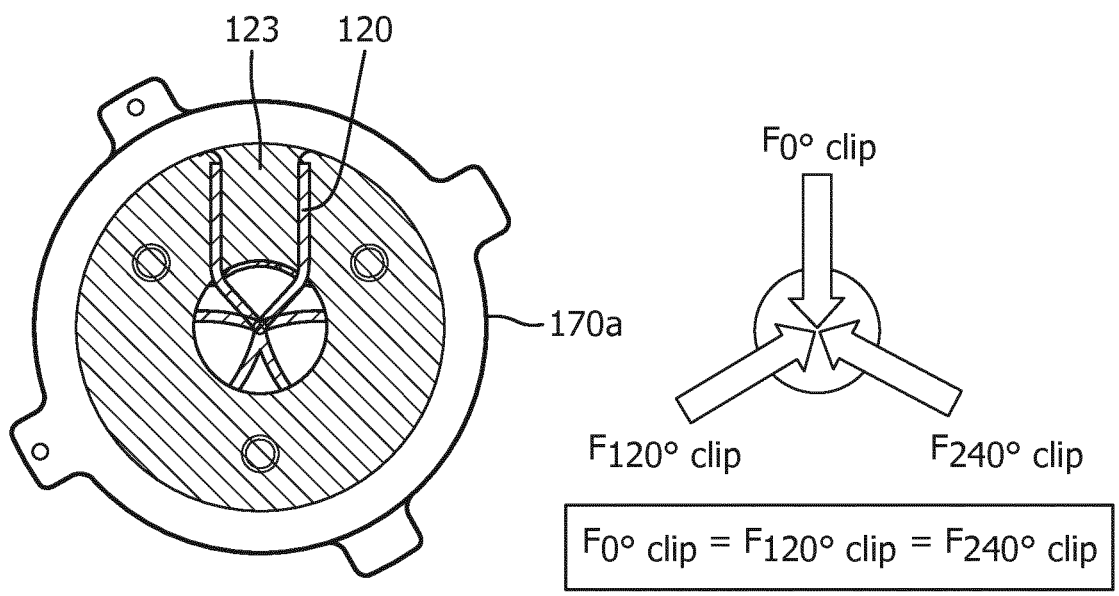
FIG. 11 is a cross-section of a pivot bearing frame and pivot bearings, in accordance with an embodiment.

Referring to FIG. 11 is a cross-section of pivot frame 170a along axis B/B in FIG. 10. The three pivot bearing clips 120 at this end of the shaft have been inserted, and the apex of each of the bearings extends into the center space of the frame where the shaft would be located. Each apex would extend into a notch 122 of the shaft in this region. As shown in the force diagram, the three bearings combined exert the proper force on the shaft 24 to keep it properly positioned and to allow it to easily and noiselessly oscillate.

Figure 12:
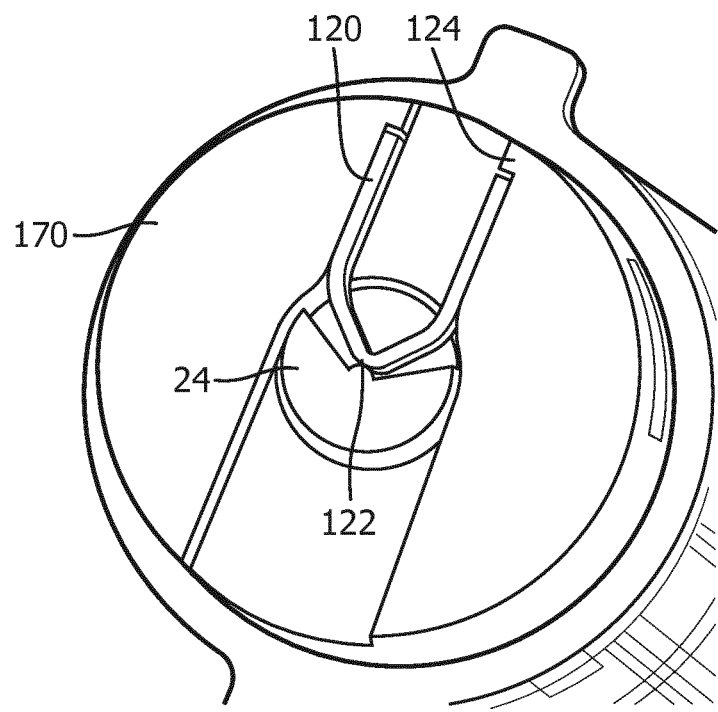
FIG. 12 is a cross-section of a pivot bearing frame, pivot bearing, and shaft, in accordance with an embodiment.

The pivot frames may take many shapes and configurations. Referring to FIG. 12, in one embodiment, is a similar cross-section of pivot frame 170. According to this embodiment, the pivot frame may comprise a locking feature 124, which in this embodiment is a ridge or ledge which is positioned at or just above the end of the pivot bearing 120 opposite the apex. This locks the pivot bearing 120 into place, with the apex of the pivot bearing 120 properly positioned in and interacting with the notch 122 of the shaft 24.

Figure 13:
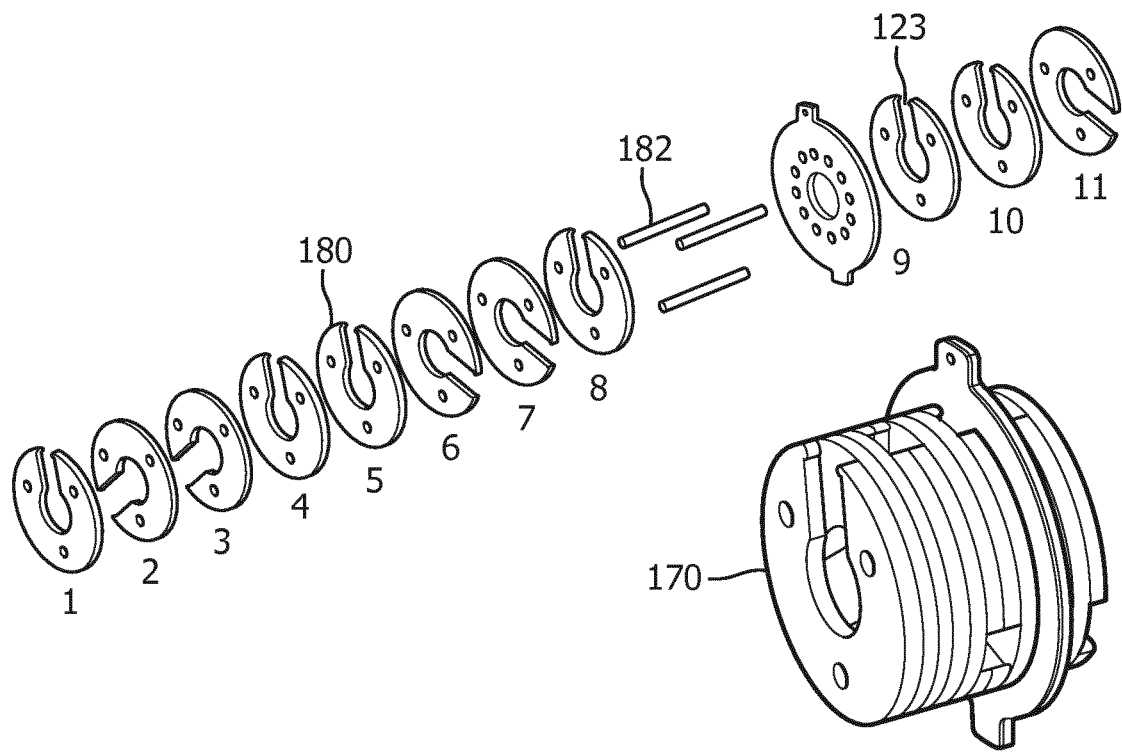
FIG. 13 is a schematic representation of a pivot bearing frame, in accordance with an embodiment.

Another configuration of the pivot frame 170 is depicted in FIG. 13. According to this embodiment, each pivot frame 170 is composed of a plurality of pivot frame plates 180, each or some of which comprise a portion of the one or more notches 123 for the pivot bearing. In this particular embodiment, two of the pivot frame plates 180 together form a notch 123 with the proper width for the pivot bearing 120. The plurality of pivot frame plates 180 can be held together, for example, by one or more pivot frame pins 182, among many other methods.

Figure 14:
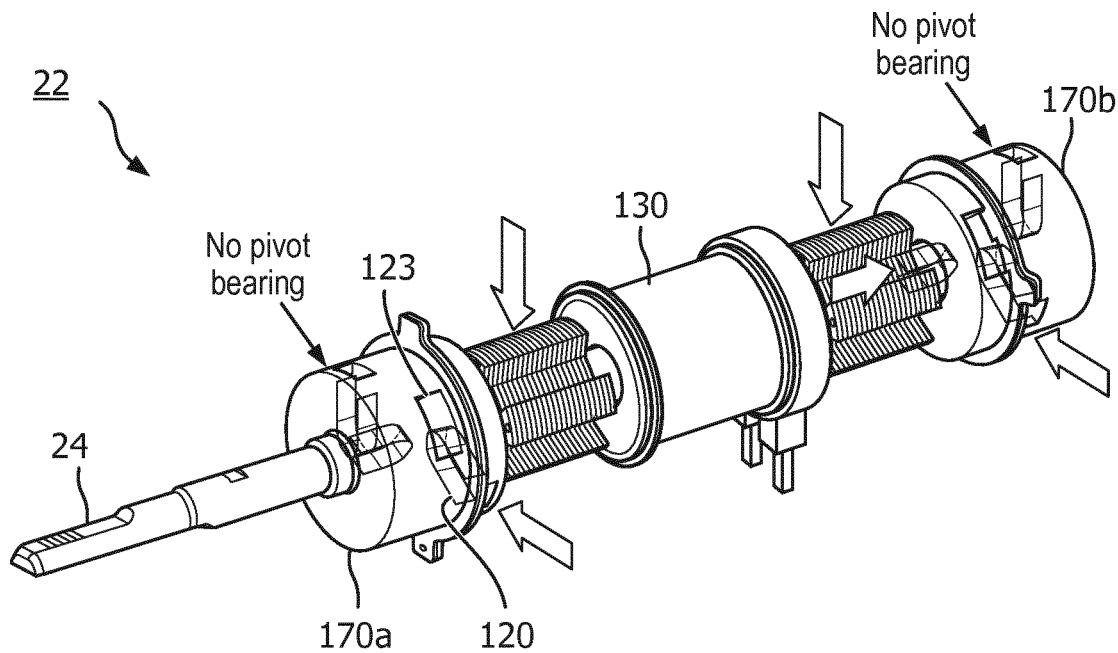
FIG. 14 is a schematic representation of a drive train assembly of an oral cleaning device, in accordance with an embodiment.
Figure 15:
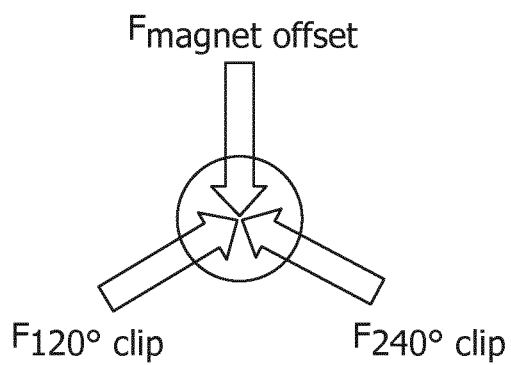
FIG. 15 is a schematic representation of the pivot bearing and magnetic offset forces exerted on a shaft, in accordance with an embodiment.

According to another embodiment, the drive shaft assembly can combine magnetic force with pivot bearings to align the shaft 24. Referring to FIG. 14, in one embodiment, is a drive shaft assembly 22. The drive shaft assembly comprises a shaft 24, a motor or drive 130, and two pivot frames 170a and 170b comprising notches 123 for pivot bearings 120. In contrast to other embodiments, the drive shaft assembly 22 comprises an internal magnetic force which opposes the force exerted by four pivot bearing clips, two each in the embodiment shown, offset by approximately 120 degrees, as shown in FIG. 15. While each of the two notches 123 in the pivot frame constrain radial forces 120 degrees offset from each other, the third direction of force, offset once again by 120 degrees, comes from a magnetic force generated inside the motor by an offset of core material. This third force is strong enough to maintain the shaft position throughout its operating loads and use scenarios. According to an embodiment, the inside diameter of the frame is selected such that it provides a hard stop against radial movement to prevent motor damage.

The drive shaft assemblies described or otherwise envisioned herein can be manufactured and assembled multiple different ways. For example, the shaft 24 can machined, with the shaft bearing pockets machined into a turned shaft. According to this embodiment, the roundness of such a shaft is no longer required for bearing purposes, which could further reduce cost. The shaft 24 can also stamped and/or cold formed iron with local precision interface for the bearing surfaces.

The pivot bearings 120 can be stamped and integrated into the motor end caps, or sintered and integrated into the end caps. According to another embodiment, the pivot bearings are cold-formed brass or bronze. The pivot bearings can also be a plastic, such as PTFE-filled POM, among many other types of plastic or polymers.

According to an embodiment, the drive shaft assemblies described or otherwise envisioned herein can be assembled via the following steps. First, the component parts are manufactured. Next, the motor end caps slide onto the shaft assembly. The bearings are then positioned, such as by snapping them into the notches of the end caps. The motor enclosure is then positioned around the shaft to apply the preload. According to an embodiment, the motor enclosure is two different halves which are then welded or otherwise connected together and/or to the end caps to form the drive train assembly. Many other methods of assembly are possible.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A drive train assembly for a personal care device, the drive train assembly comprising:
    a shaft comprising a central axis and a plurality of pivot bearing notches;
    a motor encircling at least a portion of the shaft and configured to oscillate the shaft about the shaft's central axis; and a plurality of stationary pivot bearings, wherein at least an apex of each of the plurality of stationary pivot bearings is positioned within a respective one of the plurality of pivot bearing notches.

2. The drive train assembly of claim 1, wherein a first subset of the plurality of stationary pivot bearings are positioned at a first end of the motor, and further wherein a second subset of the plurality of stationary pivot bearings are positioned at a second end of the motor.

3. The drive train assembly of claim 2, wherein the first subset and second subset each comprises three pivot bearings positioned around the shaft, and further wherein the apex of each of the three pivot bearings is offset by approximately 120 degrees from the apex of the neighboring pivot bearings.

4. The drive train assembly of claim 1, wherein the apex of each of the plurality of pivot bearing notches is positioned at the drive shaft's central axis.

5. The drive train assembly of claim 1, further comprising a first pivot bearing frame located at a first end of the motor and a second pivot bearing frame located at a second end of the motor, wherein the first pivot bearing frame and the second pivot bearing frame each comprise a plurality of pivot frame notches, and further wherein each of the plurality of pivot frame notches is configured to align with one of the plurality of pivot bearing notches.

6. The drive train assembly of claim 5, wherein the plurality of pivot frame notches each comprise a locking mechanism configured to affix the pivot bearing in place.

7. The drive train assembly of claim 5, wherein the first and second pivot bearing frames each comprises a plurality of pivot bearing frame plates.

8. The drive train assembly of claim 1, wherein the apex of the pivot bearing is pointed or curved.

9. The drive train assembly of claim 1, wherein the pivot bearing is a butterfly clip.

10. The drive train assembly of claim 1, further comprising a magnetic force exerted on the shaft, wherein the direction of the magnetic force opposes the forces exerted by the plurality of pivot bearings on the shaft.

11. A personal care device comprising:
a housing; and
a drive train assembly comprising a shaft comprising a central axis and a plurality of pivot bearing notches; a motor configured to oscillate the shaft about the shaft's central axis;
and a plurality of stationary pivot bearings, wherein at least an apex of each of the plurality of stationary pivot bearings is positioned within a respective one of the plurality of pivot bearing notches.

12. The personal care device of claim 11, wherein the drive train assembly further comprises a first pivot bearing frame located at a first end of the motor and a second pivot bearing frame located at a second end of the motor, wherein the first pivot bearing frame and the second pivot bearing frame each comprise a plurality of pivot frame notches, and further wherein each of the plurality of pivot frame notches is configured to align with one of the plurality of pivot bearing notches.

13. The personal care device of claim 11, further comprising a magnetic force exerted on the shaft, wherein the direction of the magnetic force opposes the forces exerted by the plurality of pivot bearings on the shaft.

14. A drive train assembly for a personal care device (10), the drive train assembly comprising:
a shaft comprising a central axis and a plurality of pivot bearing notches, wherein the apex of each of the plurality of pivot bearing notches is positioned at the shaft's central axis;
a motor configured to oscillate the shaft about the shaft's central axis;
a first pivot bearing frame located at a first end of the motor and comprising a first plurality of pivot frame notches;
a second pivot bearing frame located at a second end of the motor and comprising a second plurality of pivot frame notches, wherein each of the first and second plurality of pivot frame notches is configured to align with one of the plurality of pivot bearing notches; and
a plurality of stationary pivot bearings, wherein at least an apex of each of the plurality of stationary pivot bearings is positioned within a respective one of the plurality of pivot bearing notches, wherein a first subset of the plurality of stationary pivot bearings are positioned at a first end of the motor, and further wherein a second subset of the plurality of stationary pivot bearings are positioned at a second end of the motor.

15. The drive train assembly of claim 14, further comprising a magnetic force exerted on the shaft, wherein the direction of the magnetic force opposes the forces exerted by the plurality of pivot bearings on the shaft.

* * * * *